United States Patent [19]

Wight et al.

[11] 4,130,578

[45] Dec. 19, 1978

[54] IMMUNOSUPPRESSIVE DITHIOCARBANILATES

[75] Inventors: Hewitt G. Wight; Tracey G. Call, both of San Luis Obispo, Calif.; Marvin L. Mortensen, Kila, Mont.

[73] Assignee: The Upjohn Company, Kalamazoo, Mich.

[21] Appl. No.: 848,433

[22] Filed: Nov. 4, 1977

Related U.S. Application Data

[63] Continuation-in-part of Ser. No. 773,064, Feb. 28, 1977, Pat. No. 4,110,444, which is a continuation-in-part of Ser. No. 579,449, May 21, 1975, abandoned.

[51] Int. Cl.$^2$ ............................................. C07C 153/09
[52] U.S. Cl. ................................................. 260/455 A
[58] Field of Search ..................................... 260/455 A

[56] References Cited

U.S. PATENT DOCUMENTS

| | | | |
|---|---|---|---|
| 3,686,413 | 8/1972 | Hollrah | 424/300 |
| 3,781,434 | 12/1973 | Berkoff et al. | 424/246 |

FOREIGN PATENT DOCUMENTS 1153487  5/1969  United Kingdom.

*Primary Examiner*—Elbert L. Roberts
*Assistant Examiner*—Robert C. W. Whittenbaugh
*Attorney, Agent, or Firm*—Robert A. Armitage

[57] ABSTRACT

The present invention provides certain novel ω-(alkoxycarbonyl)alkyl esters of dithiocarbanilic acid and certain aryl-substituted acids related thereto. These compounds are disclosed as immunoregulatory agents, useful in the treatment of organ transplant reject phenomena and autoimmune diseases such as arthritis.

Additionally, there is described by the present invention the immunoregulatory use of ω-carboxyalkyl and ω-(alkoxycarbonyl)alkyl esters of dithiocarbanilic acid and certain aryl-substituted acids related thereto.

6 Claims, No Drawings

IMMUNOSUPPRESSIVE DITHIOCARBANILATES

CROSS REFERENCE TO RELATED APPLICATIONS

This application is a continuation-in-part of Ser. No. 773,064, filed Feb. 28, 1977, now U.S. Pat. No. 4,110,444, which is a continuation-in-part of Ser. No. 579,449, filed May 21, 1975, now abandoned.

BACKGROUND OF THE INVENTION

The present invention provides certain novel organic compounds which have immunoregulatory properties, rendering these compounds useful in the treatment of hyperimmunity diseases. Moreover, the present invention provides for the immunoregulatory use of certain organic compounds in hyperimmunity diseases.

The novel compounds herein and the compounds employed in the novel methods herein as pharmacologic agents are all thioesters of dithiocarbanilic acid or corresponding aryl-substituted dithiocarbanilic acids. Dithiocarbanilic acid has the structural formula:

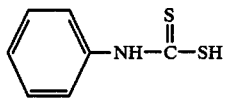
I and corresponding aryl substituted dithiocarbanilic acids include compounds of the structural formula:

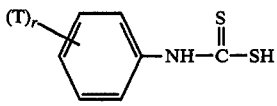
II wherein T is nitro, fluoro, chloro, bromo, trifluoromethyl, lower alkylsulphonyl, phenylsulphonyl, or (lower alkyl)phenylsulphonyl; and
wherein r is the integer 1 or 2.

The thioesters referred to above include ω-carboxyalkyl esters derived structurally from thiols of the formula

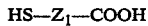    III wherein $Z_1$ is $-C_mH_{2m}-$, wherein m is the integer 1 to 5, inclusive; and ω-(alkoxycarbonyl) esters derived structurally from thiols of the formula

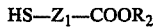    IV wherein $R_2$ is alkyl of 1 to 12 carbon atoms, inclusive; and
wherein $Z_1$ is as defined above.

Certain of the ω-carboxyalkyl esters of various dithiocarbanilic acids are known in the art as useful for a wide variety of purposes.

See, for example, Garraway, J. L., J. Chem. Soc. 1961: 3733 which describes the ω-carboxyalkyl dithiocarbanilates as precursors for the corresponding cyclic lactams (i.e., rhodanines and thiazine analogs). Further with respect to the production of rhodanine or thiazine analogs from corresponding ω-carboxyalkyl dithiocarbanilate precursors, see U.S. Pat. No. 3,781,434; Brown, F. C., et al., J.A.C.S. 78: 384 (1956); and Werbel, L. M., et al., J. Med. Chem. 11(2):364 (1968). The former reference describes the antiarthritic use of the cyclic thiazines, while the latter references describe the cyclic rhodanine derivations as antifungicidal, antibacterial, and antimalarial agents.

ω-Carboxymethyl 2,3-dihalo-dithiocarbanilates are described in British published specification No. 1,153,487 as anthelmintics. Further, U.S. Pat. No. 3,089,877 describes ω-(amidocarbonyl)alkyl dithiocarbonylates as fungicidal agents. Finally, U.S. Pat. No. 3,686,413 describes the anthelmintic use of dithiocarbanilates, including, inter alia, compounds of the formula

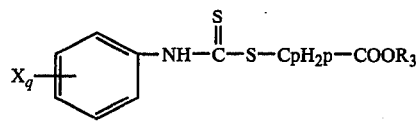

wherein $R_3$ is hydrogen or alkyl of 1 to 4 carbon atoms, inclusive;
wherein p is the integer 1 or 2;
wherein X is chloro, bromo, or nitro; and
wherein q is the integer 0 to 5, inclusive.

In addition to the uses of the dithiocarbanilates described above, certain chemical and biological investigations relating to such compounds have been undertaken and are reported in papers deposited in The California Polytechnic State University Library in San Luis Obispo, Calif. These papers are identified by author and title, as follows: Bello, J., "Some Effects of Newly Synthesized Thiocarbamates on Blood and Organ Parameters in the Mouse and Pig"; Booth, J., "The Effects of 3-(N-Meta Fluorophenyl Dithiocarbamoyl) Propanoic Acid on BAPN Induced Lathyrism in the Rat"; Burdick. P. R., "Warfarin Activity Modification and Other Effects of Some New Thiocarbamates in Mice"; Foster, R., "Modification of the Erythrocyte Membrane in Swine"; Jones, P., "Histological Effects of Carbamate Derivatives on the Spleen and Thymus of Swiss-Webster Mice"; Lash, L. D., "Leukocyte Depression and Other Responses in the Mouse, Produced by Datisca and a Novel Thiocarbamate"; Meyer, O., "The Effects of 3(N-Metafluorophenyl)Dithiocarbamoyl Propanoic Acid on the Lathrytic Condition Induced by Beta-Aminoproprionitrile"; Mortensen, M. L., "The Synthesis of Some of the Reaction Products of Isocyanates and Isothiocyanates with 3-Mercaptopropionic Acid"; and Reid, A., "Modification of Lathyrism in Rats by Three New Thiocarbamates."

Immunoregulatory agents may be either immunosuppressive or immunostimulatory. For the purposes of the present invention immunoregulation shall make reference to the process of immunosuppression in response to a disease or other condition resulting from hyperimmunity in the animal or patient. For a comprehensive review of the use of immunosuppressive agents in the treatment of hyperimmunity diseases, see Camiener, G. W., et al., Progress in Drug Research 16:67 (1972) and Wechter, W. J., et al., Progress in Drug Research 20:573 (1976).

Many known immunosuppressive agents are cytotoxic and are believed in part to accomplish the immunosuppressive effects via a cytotoxic mechanism on the immunoactive organs (e.g., bone marrow and thymus). For example, the known antineoplastic agent, cyclophosphamide, has been used in the treatment of arthritis. See Skinner, M. D., et al., Rheumatology 5:1 (1974).

Finally, anthelmintics such as niridazole have been employed immunosuppressively to control allograft rejection; while another anthelmintic, levamisole, is apparently a non-specific stimulator of the immune system. See Daniels, J. D., et al., J. Immun. 115:1414 (1975) and Renorex, G., et al., J. Immun. 109:761 (1972).

SUMMARY OF THE INVENTION

The present invention provides novel organic compounds and methods for their use as pharmaceutical agents. Further, the present invention comprises the immunosuppressive use of certain dithiocarbanilates.

In particular, the present invention provides:
(A) a compound of the formula

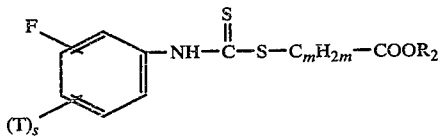

wherein T is nitro, fluoro, chloro, bromo, trifluoromethyl, lower alkylsulphonyl, phenylsulphonyl, or (lower alkyl)phenylsulphonyl;
wherein s is the integer 0 or 1;
wherein $C_mH_{2m}$ is alkylene of 1 to 5 carbon atoms, inclusive; and
wherein $R_2$ is alkyl of 1 to 12 carbon atoms, inclusive;
(B) a compound of the formula

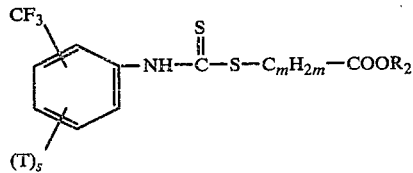

wherein T, s, $C_mH_{2m}$, and $R_2$ are as defined above;
(C) a compound of the formula

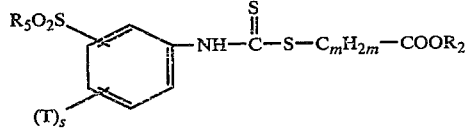

wherein T, s, $C_mH_{2m}$, and $R_2$ are as defined above; and
wherein $R_5$ is alkyl of 1 to 4 carbon atoms, inclusive; or
(D) a compound of the formula

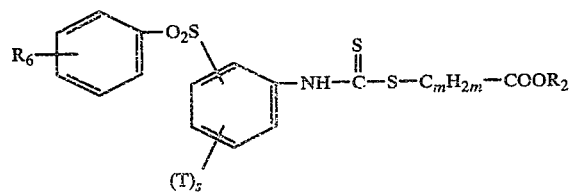

wherein T, s, $C_mH_{2m}$, and $R_2$ are as defined above; and
wherein $R_6$ is hydrogen or alkyl of 1 to 4 carbon atoms, inclusive.

The further particulars of the present invention include
(E) a method of producing immunosuppression in a mammal exhibiting a hyperimmunity disease which comprises
systemically administrating in a pharmaceutically acceptable dosage form a dithiocarbanilate of the formula

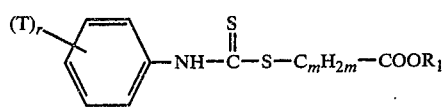

wherein T, r, and $C_mH_{2m}$ are as defined above, and $R_1$ is hydrogen or $R_2$;
in an amount effective to ameliorate or cure said hyperimmunity disease.

The novel ω-(alkoxycarbonyl)alkyl dithiocarbanilates are characterized by fluoro, trifluoromethyl, alkylsulphonyl, or arylsulphonyl substitution on the phenyl ring, and hence such novel compounds are respectively named as ω-(alkoxycarbonyl)alkyl:

o-, m-, or p-fluorodithiocarbanilates,
o-, m-, or p-(trifluoromethyl)dithiocarbanilates,
o-, m-, or p-(alkylsulphonyl)-dithiocarbanilates, or
o-, m-, or p-(arylsulphonyl)dithiocarbanilates.

When s is the integer 1, the corresponding disubstituted dithiocarbanilates are described.

For those novel ω-(alkoxycarbonyl)alkyl dithiocarbanilates wherein the integer s is 1, disubstituted dithiocarbanilates are thusly described.

For the novel fluoro-substituted dithiocarbanilates described above, the corresponding disubstituted compounds include ω-(alkoxycarbonyl)alkyl:

2,3-; 2,4-; 2,5-; 3,4-; or 3,5-difluorodithiocarbanilates;
2-fluoro-3-, 4-, or 5-trifluoromethyldithiocarbanilates;
3-fluoro-4-, or 5-trifluoromethyldithiocarbanilates;
4-fluoro-5-trifluoromethyldithiocarbanilates;
2-fluoro-3-, 4-, or 5-nitrodithiocarbanilates;
3-fluoro-4-, or 5-nitrodithiocarbanilates;
4-fluoro-5-nitrodithiocarbanilates;
2-fluoro-3-, 4-, or 5-chlorodithiocarbanilates;
3-fluoro-4-, or 5-chlorodithiocarbanilates;
4-fluoro-5-chlorodithiocarbanilates;
2-fluoro-3-, 4-, or 5-bromodithiocarbanilates;
3-fluoro-4-, or 5-bromodithiocarbanilates;
4-fluoro-5-bromodithiocarbanilates;
2-fluoro-3-, 4-, or 5-alkylsulfonyldithiocarbanilates;
3-fluoro-4-, or 5-alkylsulfonyldithiocarbanilates;
4-fluoro-5-alkylsulphonyldithiocarbonates;
2-fluoro-3-, 4-, or 5-arylsulphonyldithiocarbanilates;
3-fluoro-4-, or 5-arylsulphonyldithiocarbanilates; or
4-fluoro-5-arylsulphonyldithiocarbanilates.

For the novel trifluoromethyl-substituted dithiocarbanilates described above, the corresponding disubstituted compounds include, in addition to those listed above, ω-(alkoxycarbonyl)alkyl:
2,3-; 2,4-; 2,5-; 3,4-; or 3,5-di(trifluoromethyl)dithiocarbanilates;
2-trifluoromethyl-3-, 4-, or 5-nitrodithiocarbanilates;

3-trifluoromethyl-4-, or 5-nitrodithiocarbanilates;
4-trifluoromethyl-5-nitrodithiocarbanilates;
2-trifluoromethyl-3-, 4-, or 5-chlorodithiocarbanilates;
3-trifluoromethyl-4-, or 5-chlorodithiocarbanilates;
4-trifluoromethyl-5-chlorodithiocarbanilates;
2-trifluoromethyl-3-, 4-, or 5-bromodithiocarbanilates;
3-trifluoromethyl-4-, or 5-bromodithiocarbanilates;
4-trifluoromethyl-5-bromodithiocarbanilates;
2-trifluoromethyl-3-, 4-, or 5-alkylsulphonyldithiocarbanilates;
3-trifluoromethyl-4-, or 5-alkylsulphonyldithiocarbanilates;
4-trifluoromethyl-5-alkylsulphonyldithiocarbanilates;
2-trifluoromethyl-3-, 4-, or 5-arylsulphonyldithiocarbanilates;
3-trifluoromethyl-4-, or 5-arylsulphonyldithiocarbanilates; or
4-trifluoromethyl-5-arylsulphonyldithiocarbanilates.

For the novel alkylsulphonyl substituted dithiocarbanilates described above, the corresponding disubstituted compounds include, in addition to those listed above ω-(alkoxycarbonyl)alkyl:

2,3-; 2,4-; 2,5-; 3,4-; or 3,5-di(alkylsulphonyl)dithiocarbanilates;
2-alkylsulphonyl-3-, 4-, or 5-nitrodithiocarbanilates;
3-alkylsulphonyl-4-, or 5-nitrodithiocarbanilates;
4-alkylsulphonyl-5-nitrodithiocarbanilates;
2-alkylsulphonyl-3-, 4-, or 5-chlorodithiocarbanilates;
3-alkylsulphonyl-4-, or 5-chlorodithiocarbanilates;
4-alkylsulphonyl-5-chlorodithiocarbanilates;
2-alkylsulphonyl-3-, 4-, or 5-bromodithiocarbanilates;
3-alkylsulphonyl-4-, or 5-bromodithiocarbanilates;
4-alkylsulphonyl-5-bromodithiocarbanilates;
2-alkylsulphonyl-3-, 4-, or 5-arylsulphonyldithiocarbanilates;
3-alkylsulphonyl-4-, or 5-arylsulphonyldithiocarbanilates; or
4-alkylsulphonyl-5-arylsulphonyldithiocarbanilates.

For the novel arylsulphonyl-substituted dithiocarbanilates described above, the corresponding disubstituted compounds include, in addition to those listed above, ω-(alkoxycarbonyl)alkyl:

2,3-; 2,4-; 2,5-; 3,4-; or 3,5-di(arylsulphonyl)dithiocarbanilates;
2-arylsulphonyl-3-, 4-, or 5-nitrodithiocarbanilates;
3-arylsulphonyl-4-, or 5-nitrodithiocarbanilates;
4-arylsulphonyl-5-nitrodithiocarbanilates;
2-arylsulphonyl-3-, 4-, or 5-chlorodithiocarbanilates;
3-arylsulphonyl-4-, or 5-chlorodithiocarbanilates;
4-arylsulphonyl-5-chlorodithiocarbanilates;
2-arylsulphonyl-3-, 4-, or 5-bromodithiocarbanilates;
3-arylsulphonyl-4-, or 5-bromodithiocarbanilates; or
4-arylsulphonyl-5-bromodithiocarbanilates.

With respect to the alkylsulphonyl-substituted dithiocarbanilates referred to above, there are included methylsulphonyl, ethylsulphonyl, n-propylsulphonyl, isopropylsulphonyl, n-butylsulphonyl, isobutylsulphonyl, and tert-butylsulphonyl moieties.

With respect to the arylsulphonyl-substituted dithiocarbanilates described above, reference is made to the phenylsulphonyl and (lower alkyl)phenylsulphonyl moieties, including methylphenylsulphonyl, ethylphenylsulphonyl, n-propylphenylsulphonyl, isopropylphenylsulphonyl, n-butyl-phenylsulphonyl, isobutylphenylsulphonyl, and tert-butyl-phenylsulphonyl. With respect to such arylsulphonyl moieties, preferred compounds include mesyl (methylsulphonyl) and tosyl (p-toluenesulphonyl).

With respect to the ω-(alkoxycarbonyl)alkyl esters, $R_2$ includes methyl, ethyl, propyl, butyl, pentyl, hexyl, heptyl, octyl, nonyl, decyl, undecyl, dodecyl, and the isomeric forms thereof. Especially preferred are compounds wherein $R_2$ is lower alkyl (methyl, ethyl, propyl, or butyl), with those compounds wherein $R_2$ is methyl or ethyl being most preferred. With respect to $-C_mH_{2m}-$, preferred compounds are those wherein this moiety is methylene, ethylene, or methyl-substituted ethylene.

In accordance with these preferences described above, the preferred ω-(alkoxycarbonyl)alkyl esters include ω-(methoxycarbonyl)methyl, ω-(ethoxycarbonyl)methyl, ω-(propoxycarbonylmethyl, ω-(butoxycarbonyl)methyl, ω-(methoxycarbonyl)ethyl, ω-(ethoxycarbonyl)ethyl, ω-(propoxycarbonyl)ethyl, ω-(butoxycarbonyl)ethyl, 2-(methoxycarbonyl)-1-methyl-ethyl, 2-(ethoxycarbonyl)-1-methyl-ethyl, 2-(propoxycarbonyl)-1-methylethyl, and 2-(butoxycarbonyl)-1-methyl-ethyl.

The novel ω-(alkoxycarbonyl)dithiocarbanilates of the present invention are prepared by methods analogous to those known in the art. For example, see the methods referred to in U.S. Pat. Nos. 3,686,413 and 3,781,434, described above. Accordingly, the compounds of the present invention are prepared by reacting the appropriate arylisothiocyanate with the appropriate ω-(carboxycarbonyl)alkylthiol. The reaction proceeds at ambient temperature, being slightly exothermic, and is ordinarily complete within about 1 hour. Preferred reaction solvents are anhydrous, nonpolar organic solvents such as benzene, xylene, or toluene. Recovery of the novel reaction product proceeds by conventional means, e.g., evaporation of solvent. The required starting materials for the present transformations are readily available or synthesized by readily available means.

With respect to the novel method described above for producing immunosuppression in mammals exhibiting hyperimmunity disease, the use of this method in man is especially intended. However, the use in valuable domestic animals, such as canine, feline, bovine, and equine species is further intended.

Hyperimmunity diseases encompassed by the present method include transplant rejection phenomena and autoimmune diseases.

With respect to the transplant rejection phenomena, the present invention relates to allograph rejection phenomena in organ transplantation, including graph-versus-host disease in allographic bone marrow transplantation.

With regard to the autoimmune diseases encompassed by the present method, there is included rheumatoid arthritis, psoriatic arthritis, systemic lupus erythematosus, regional enteritis, chronic active hepatitis, nephrotic syndrome, glomerulonephritis, lupus nephritis, and ulcerative colitis.

In the use of the present invention in transplant rejection phenomena, advantageous results ranging from prolongation of the viability of the transplanted tissue to complete cessation of the rejection process are obtained. In the treatment of autoimmune diseases by the present method, advantageous results ranging from significant symptomatic relief to cessation of the underlying inflammatory process are obtained.

In the treatment of the hyperimmunity diseases described above, the requisite clinical endpoint is the suppression of the mammal's immune response, thereby effecting amelioration or cure of the hyperimmunity disease. Accordingly, the present invention contemplates use of effective dosages of the dithiocarbanilate such that the disease progress is first halted and thereafter reversed. The amount of dithiocarbanilate required depends upon a wide variety of factors including the particular compound selected, the age, weight and condition of the mammal being treated, the severity of the particular hyperimmune disease being treated, and the response of the mammal to treatment.

In order to obtain the efficacious results provided by the present invention, any systemic route of administration is acceptable. However, for convenience, the preferred route of administration is orally, although other systemic routes of administration provide equivalent activity at the appropriate dose. Thus, intravenous injection or infusion, subcutaneous injection, or administration in the form of rectal or vaginal suppository represent alternate routes of administration. Regardless of the route of administration selected, the dithiocarbanilate is formulated in a pharmaceutically acceptable dosage form by conventional methods available in the pharmaceutical arts.

Accordingly, when compressed tablets are desired for oral administration, the dithiocarbanilate is combined with the desired inert ingredients and thereafter compressed by conventional means into a tablet containing the desired quantity of dithiocarbanilate. In the case of parenteral administration, sterile solutions for injection or infusion are prepared in accordance with readily available techniques.

After the onset of the hyperimmunity disease has been diagnosed by the attending physician or veterinarian, the treatment with the dithiocarbanilate in accordance with the present method may be initiated promptly. In cases where the dithiocarbanilate is the sole immunosuppressive agent to be employed in the treatment of the hyperimmunity disease, an initial dosage between 0.5 and 50 mg/kg/day is employed. When initial dosages at the lower end of the above range are employed, the mammal's progress is monitored and dosages on subsequent days are increased in the event that the patient or animal response is deemed by the attending physician or veterinarian to be absent or insufficient. When dosages as high as about 50 mg/kg/day are selected, the systemic toxicity of the dithiocarbanilate must be carefully evaluated and subsequent dosages determined by evaluating the benefits of the drug in relationship to any such toxic manifestations.

For convenience, dosages may be administered once daily or, more preferably, administered at periodic intervals throughout the day. Accordingly, in man the dithiocarbanilate is advantageously administered at 4 or 8 hr. intervals throughout the day.

Accordingly, the present method provides a new and unexpected use for a class of dithiocarbanilates previously known to be useful for unrelated purposes. Additionally, the present invention provides new and structurally distinct ω-(alkoxycarbonyl)alkyl dithiocarbanilates which in accordance with the present invention surprisingly and unexpectedly exhibit immunosuppressive properties rendering them useful in the treatment of hyperimmunity diseases.

Moreover, of the various dithiocarbanilates described herein as immunosuppressive the novel ω-(alkoxycarbonyl)alkyl dithiocarbanilates represent an especially preferred class of immunosuppressive agents, particularly being preferred for certain purposes over use of the corresponding ω-carboxyalkyl dithiocarbanilates. For example, in the preparation, formulation and storage of the ω-(alkoxycarboxy)alkyl dithiocarbanilates, these novel compounds exhibit a prolonged stability and are less likely to chemically rearrange to cyclic derivatives than the ω-carboxyalkyl compounds.

Finally, the unique chemical structure of these ω-(alkoxycarbonyl)alkyl dithiocarbanilates provides these compounds with advantageous absorption characteristics, resulting in more prolonged immunosuppressive activity with fewer undesired systemic effects.

DESCRIPTION OF THE PREFERRED EMBODIMENTS

EXAMPLE 1

ω-(methoxycarbonyl)ethyl m-fluorodithiocarbanilate

In a benzene solvent equal molar amounts of ω-(methoxycarbonyl)ethylthiol and m-fluorophenylisothiocyanate are stirred for about 1 hr. at ambient temperature. The resulting title product is thereafter obtained by solvent evaporation.

Following the procedure of Example 1, but using the corresponding o-fluoro- or p-fluoro-phenylisocyanates, there is obtained a corresponding product: ω-(methoxycarbonyl)ethyl o-fluorodithiocarbanilate or p-fluorodithiocarbanilate.

Employing the corresponding trifluoromethyl substituted phenylisocyanates, there are obtained the corresponding ω-(methoxycarbonyl)ethyl trifluoromethyl-substituted dithiocarbanilates.

Likewise following the procedure of Example 1, but employing the corresponding ω-(ethoxycarbonyl)ethyl or ω-(propoxycarbonyl)ethylthiol in place of ω-(methoxycarbonyl) ethylthio, there are obtained the corresponding ω-(ethoxycarbonyl)ethyl or ω-(propoxycarbonyl)ethyl fluoro-substituted dithiocarbanilates. Further following the procedure of Example 1 but employing the corresponding ω-(methoxycarbonyl)methylthiol in place of ω-(methoxycarbonyl)ethylthio, there are obtained the corresponding ω-(methoxycarbonyl)-methyl fluoro-substituted dithiocarbanilates. Likewise, employing corresponding 2-(methoxycarbonyl)-1-methyl-ethylthiol in place of ω-(methoxycarbonyl)ethylthiol, there is obtained 2-(methoxycarbonyl)-1-methyl-ethyl fluoro-substituted dithiocarbanilates.

Accordingly, Example 1 describes the manner of preparation of the various novel dithiocarbanilates described in accordance with the present invention.

We claim:

1. A compound of the formula

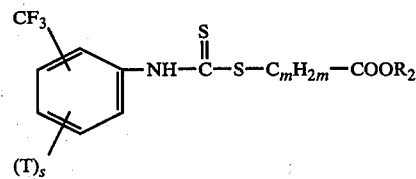

wherein T is nitro, fluoro, chloro, bromo, trifluoromethyl, lower alkylsulphonyl, phenylsulphonyl, or (lower alkyl)phenylsulphonyl;
wherein s is the integer 0 or 1;
wherein $C_mH_{2m}$ is alkylene of 1 to 5 carbon atoms, inclusive; and
wherein $R_2$ is alkyl of 1 to 12 carbon atoms, inclusive.

2. ω-(Methoxycarbonyl)ethyl m-(trifluoromethyl)dithiocarbanilate, a compound according to claim 1.

3. A compound of the formula

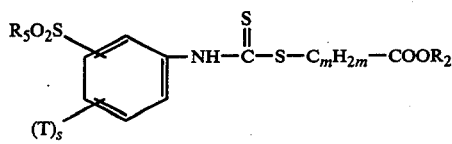

wherein T is nitro, fluoro, chloro, bromo, trifluoromethyl, lower alkylsulphonyl, phenylsulphonyl, or (lower alkyl)phenylsulphonyl;
wherein s is the integer 0 or 1;
wherein $C_mH_{2m}$ is alkylene of 1 to 5 carbon atoms, inclusive;
wherein $R_2$ is alkyl of 1 to 12 carbon atoms, inclusive; and
wherein $R_5$ is alkyl of 1 to 4 carbon atoms, inclusive.

4. ω-(Methoxycarbonyl)ethyl m-(methylsulphonyl)dithiocarbanilate, a compound according to claim 3.

5. A compound of the formula

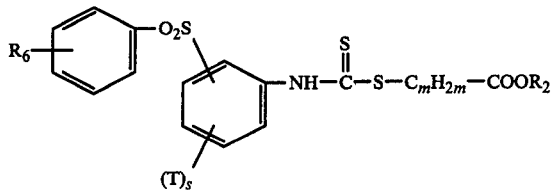

wherein T is nitro, fluoro, chloro, bromo, trifuloromethyl, lower alkylsulphonyl, phenylsulphonyl, or (lower alkyl)phenylsulphonyl;
wherein s is the integer 0 or 1;
wherein $C_mH_{2m}$ is alkylene of 1 to 5 carbon atoms, inclusive;
wherein $R_2$ is alkyl of 1 to 12 carbon atoms, inclusive; and
wherein $R_6$ is hydrogen or alkyl of one to 4 carbon atoms, inclusive.

6. ω-(Methoxycarbonyl)ethyl m-(p-toluenesulphonyl)dithiocarbanilate, a compound according to claim 5.

* * * * *

UNITED STATES PATENT OFFICE
CERTIFICATE OF CORRECTION

Patent No. 4,130,578            Dated December 19, 1978

Inventor(s) Hewitt G. Wight, Tracey G. Call, Marvin L. Mortensen

It is certified that error appears in the above-identified patent and that said Letters Patent are hereby corrected as shown below:

-- [73] Assignee: The California Polytechnic State University Foundation, San Luis Obispo, California -- instead of the assignee shown on the printed patent.

Column 2, line 2, "derivations" should read -- derivatives --; line 4, "2,3-dihalo-" should read -- 3,4-dihalo- --.

Signed and Sealed this

Twenty-second Day of May 1979

[SEAL]

Attest:

RUTH C. MASON
Attesting Officer

DONALD W. BANNER
Commissioner of Patents and Trademarks